(12) United States Patent
Sepahvand

(10) Patent No.: US 8,153,169 B1
(45) Date of Patent: Apr. 10, 2012

(54) METHOD OF PREPARING HERBAL MEDICINE FOR TREATING FEMALE INFERTILITY

(76) Inventor: Fariba Sepahvand, Khoramabad (IR)

( * ) Notice: Subject to any disclaimer, the term of this patent is extended or adjusted under 35 U.S.C. 154(b) by 0 days.

(21) Appl. No.: 13/020,819

(22) Filed: Feb. 4, 2011

(51) Int. Cl.
*A61K 36/00* (2006.01)

(52) U.S. Cl. ........ 424/725; 424/522; 424/756; 424/773; 424/776

(58) Field of Classification Search .................. 435/410; 424/725, 773, 776
See application file for complete search history.

(56) References Cited

OTHER PUBLICATIONS

Ganiger et al., A two generation reproductive toxicity study with curcumin, turmeric yellow, in Wistar rats, 2007, Food and Chemical Toxicology 45(1): 64-69.*

* cited by examiner

*Primary Examiner* — Ralph Gitomer
*Assistant Examiner* — Robert Yamasaki
(74) *Attorney, Agent, or Firm* — Barry Choobin; Choobin & Choobin Consultancy L.L.C.

(57) ABSTRACT

The various embodiments herein provide a herbal medicine for treatment of infertility in women. The medicine includes a tea-spoon of corncockle powder and a tea-spoon of turmeric powder dissolved in a sheep oil. The embodiments herein also provide a method of preparing a medicine for treatment of infertility. According to the method, a corncockle powder and a turmeric powder are prepared and mixed with an animal oil to form a liquid mixture. The mixture is kept for 24 hrs at room temperature. Moreover, the embodiments herein also provide a method of treating infertility in a patient by injecting a dose of 2 cc to 10 cc of the prepared medicine in the vagina of the patient for 3 consecutive days immediately after a completion of a menstrual cycle using a disposable or reusable syringe without a needle.

4 Claims, 1 Drawing Sheet

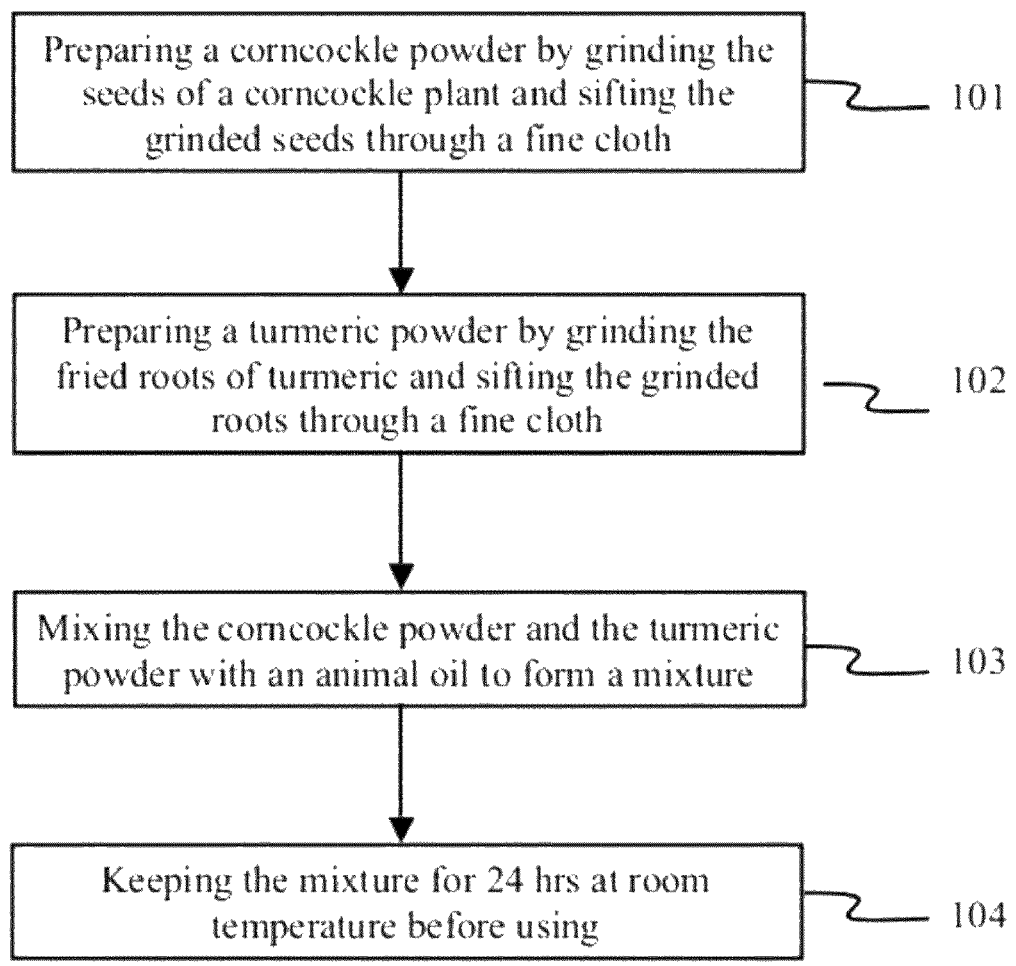

METHOD OF PREPARING HERBAL MEDICINE FOR TREATING FEMALE INFERTILITY

BACKGROUND

1. Technical Field

The embodiments herein generally relate to a method of treatment of infertility in women. The embodiments herein particularly relate to a herbal medicine and more particularly relate to a method of preparation of herbal medicine for infertility in women and a method of the treatment of infertility in women using the herbal medicine.

2. Description of the Related Art

*Agrostemma* is a genus of annual plants in the Caryophyllaceae family, containing the species known as corncockles. Its best-known member is *Agrostemma githago*, known as the Common Corncockle. The Common corncockle is an annual forb probably with a centre of origin in the eastern Mediterranean. The plant is a weed of cereals and crops. The Common Corncockle plant is a stiffly erect plant. The plant is up to 1 meter tall and is covered with fine hairs. The branches of corncockle plant are tipped with a single deep pink to purple flower. The flowers are scentless and are 25 mm to 50 mm across. The flowers are produced in the months of May to September in the northern hemisphere and in the months of November to March in southern hemisphere. Each petal bears 2 or 3 discontinuous black lines. The five narrow pointed sepals exceed the petals and are joined at the base to form a rigid tube with 10 ribs. Leaves are in pale green, opposite, narrowly lanceolate, held nearly erect against stem and are 45 mm to 145 mm long. *Agrostemma githago* is either self-fertilized or pollinated by insects. Seeds are produced in a many-seeded capsule. *Agrostemma githago* may produce over 3,000 seeds per plant and up to 60 seeds per capsule. Propagation is from seeds. Other anthers then elongate, allowing self-fertilization. Seeds are shed about a year after germination. If not harvested, the seeds fall and germinate within 1 m of the parent plants. *Agrostemma githago* produces up to 4,000 seeds/m$^2$ and approximately 3,685 seeds per plant. The whole plant contains a saponin called githagenin, which acts as a poison to many farm animals and man. The corncockle plant can be found in fields, roadsides, railway lines, waste places, and other disturbed areas. Corncockle is an attractive plant, and its seeds are still commercially available to gardeners. All parts of the plant are reported to be poisonous but it has been used in folk medicine to treat a range of ills, from parasites to cancer but it may produce chronic or acute, potentially fatal poisoning. The seeds can cause death if ingested in sufficient quantity. The plant is also cultivated as a garden ornament and used horticulturally.

*Curcuma longa*, a perennial herb and member of the Zingiberaceae (ginger) family, grows to a height of three to five feet and is cultivated extensively in Asia, India, China, and other countries with a tropical climate. It has oblong, pointed leaves and funnel-shaped yellow flowers. The rhizome, the portion of the plant used medicinally, is usually boiled, cleaned, and dried, yielding a yellow powder. Dried *Curcuma longa* is the source of the spice turmeric, the ingredient that gives curry powder its characteristic yellow color. Turmeric is used extensively in foods for its flavor and color, as well as having a long tradition of use in the Chinese and Ayurvedic systems of medicine, particularly as an anti-inflammatory and for the treatment of flatulence, jaundice, hematuria, hemorrhage, and colic. Turmeric can also be applied topically in poultices to relieve pain and inflammation. The active constituents of turmeric are the flavonoid curcumin (diferuloylmethane) and various volatile oils, including tumerone, atlantone, and zingiberone. Other constituents include sugars, proteins, and resins. The best-researched active constituent is curcumin, which comprises 0.3-5.4 percent of raw turmeric.

Infertility in women is conventionally defined as failure to conceive despite regular sexual intercourse for a year, without using any contraceptive. The period of sterility in various individuals is different. A woman's age is probably the most significant factor related to her ability to conceive. In addition to age, there are a number of conditions that can interfere with a woman's fertility, including endometriosis, polycystic ovarian syndrome, pituitary tumors and pelvic inflammatory disease. Sometimes the cause of infertility is unknown. No doubt there are various surgical and medicinal methods that cure female infertility but these methods are costly and have great side-effects.

Hence there is a need to provide an economical, cheap and effective method of treating infertility in women with unknown reasons.

The above mentioned shortcomings, disadvantages and problems are addressed herein and which will be understood by reading and studying the following specification.

OBJECTIVES OF THE EMBODIMENTS

The primary object of the embodiments herein is to provide a method of treatment of infertility in women with unknown reasons for many years.

Another object of the embodiments herein is to provide a cheap and effective method for the treatment of infertility in women.

Yet another object of the embodiments herein is to provide a method for the treatment of infertility in women without producing any side-effects.

Yet another object of the embodiments herein is to provide an effective medicine for treatment of infertility in women using a herbal medicine comprising corncockle and turmeric where the corncockle and the turmeric are working in synergism.

Yet another object of the embodiments herein is to provide a medicine that is simple and easy to make, for treatment of infertility in women.

Yet another object of the embodiments herein is to determine the pregnancy in barren women after giving medicine according to a period of sterility.

Yet another object of the embodiments herein is to determine the effect of pharmaceutical plant (herb) on curing the barren patients with unknown reason.

These and other objects and advantages of the embodiments herein will become readily apparent from the following detailed description taken in conjunction with the accompanying drawings.

SUMMARY

The various embodiments herein provide a medicine for treatment of infertility in women. The medicine includes a corncockle powder, a turmeric powder and animal oil. The corncockle powder and turmeric powder are used in combination. The corncockle powder and the turmeric powder are used in a quantity of a tea-spoon. The animal oil is sheep oil. The medicine is in a form of a liquid. The medicine is given in the vagina of the patient. The standard dose of medicine is 2 cc. The dose can be increased from 2 cc to 4 cc in some patients wherein 2 cc is in-effective. The medicine is injected inside the vagina with the help of a syringe. The syringe is a disposable or a reusable syringe.

The embodiments herein also provide a method of making a medicine for treatment of infertility. In the method, a corncockle powder prepared and a turmeric powder are prepared. A tea-spoon of the corncockle powder and a teaspoon of turmeric powder are mixed with a quantity sufficient amount of animal oil. The mixture formed is kept at room temperature for 24 hrs.

According to an embodiment herein, in the preparation of corncocokle powder, the seeds of corncockle plant are separated, dried and grinded. The grinded seeds are then sifted using a mal mal cloth to obtain a homogeneous powder. In the preparation of turmeric powder, the roots or rhizomes of the turmeric plant are stir-fried for 10 minutes till inflate. The roots are then grinded and sifted using a mal mal cloth to obtain a homogeneous powder. The corncockle powder and turmeric powder are mixed in a quantity of a teaspoon in animal oil. The animal oil is sheep oil.

According to one embodiment herein, a method of treating infertility in a patient by giving a dose of a herbal medicine is provided. The medicine is given in the vagina of the patient for first two consecutive days after the completion of the menstrual cycle of the patient. The patient does not indulge in sexual intercourse in the first two days. The patient also avoids micturition till morning after taking the medicine. For the next two consecutive days, the patient does not take medicine. The patient also avoids a sexual intercourse. On the fifth day, the patient performs a sexual intercourse and avoids taking the medicine. The patient avoids micturition till morning after having a sexual intercourse. After taking the medicine, the patient keeps her pelvic up to allow an absorption of drug inside the vagina. The patient bends her feet in 90 degrees for 40 minutes to 1 hour. The patient does not sleep for 4 to 5 hours after taking the medicine. The patient does not urinate till morning after taking the medicine and does not sleep till an elapse of 3 hours after taking the medicine. The dose of medicine is in the range of 2 cc to 10 cc and 2 cc is the standard dose. According to the embodiments herein, the dose is increased from 2 cc to 4 cc in the next month, when the first dose of 2 cc given in the first month is in-effective. The medicine is given for three consecutive nights.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which:

FIG. 1 shows a flow chart illustrating the various steps of preparing a herbal medicine for curing the infertility of a woman, according to an embodiment herein.

DETAILED DESCRIPTION OF THE EMBODIMENTS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments herein provide a method of treating infertility in women using a pharmaceutical plant, *Agrostemma githago*. The plant has curing properties in digestive, respiratory and renal diseases. The plant also has anti-convulsive properties. The seed of the plant, Nigella, has a wonderful effect on conceiving activities. The seed is used as a remedy for sterility. The seeds also have anti-tumor, anti-bacterial, anti-worm, purgative and menstrual effects. The plant is grown in the north and west-north of Iran. There is no evidence for the usage of the plant corncockle in curing the sterility of women.

The corncockle plant and the curcuma longa plant are grown in Mashhad (a city in Iran). The plants grown in this city are more effective as medicine. This medicine is used for treatment of women who suffer infertility without any clear reason. Those who have strong spermatozoon and ovum. This medicine is used after the seventh days of period. Any stain shouldn't be evident. At the first night 2 cc of the drug is injected. Dependant on the term of infertility, if the length of infertility is 5 years 2 cc may be enough. The standard doze is 2 cc.

According to the embodiments herein, the plant corncokle and *Curcuma longa* (turmeric) are used in combination. The two plants are used in synergism to earn the result of remedial for infertility. The corncokle fruit capsule is more effective and used herein. The capsule contains 30 to 40 dark-colored seeds. The dark colored seeds are used herein. The effective medical substance in common corncokle is a kind of mobile oil, called Nigellone. Nigellone is produced from the extraction of common corncokle essence. In the embodiments herein, the seeds of the plant are used.

According to the embodiments herein, when the common corncokle plant is ready to harvest, its dark seeds are separated, dried and grinded to form a powder. The powder is then sifted through a fine sieve to obtain a homogeneous powder. Mal mal cloth is used to sift the powder. The powder is used for the treatment.

According to the embodiments herein, a tea-spoon of the corncokle powder is used for the treatment of infertility in women. The common corncokle plant used should be pure. The one available in the market has impurities. So the common corncokle plant should be grown in a medical field to avoid impurities.

According to the embodiments herein, the common corncockle which exists readily in the spicery can be used for providing the medicine. The seeds must be pure.

According to an embodiment herein, the roots of curcuma longa is stir-fried for 10 minutes to inflate. Burning is avoided. After inflation, the roots of curcuma longa are poured into a mortar for grinding. After grinding the roots, the powder is sifted using a fine sieve to obtain a homogenous powder. A mal-mal cloth is used to sift the powder. The homogeneous powder obtained is used for treatment. According to the embodiments, a tea-spoon of the curcuma longa powder is used for treatment of infertility in women.

After grinding curcuma longa and common corncokle, the two powders are mixed and put in a closed glass container. Animal oil is added to the glass bottle for sublimation of the mixture. According to the embodiments herein, the proportions of both powders are equal, but the amount of oil is more than the amount of these powders to form a liquid mixture.

According to an embodiment herein, the oil is hydrogenated solid oil. The animal oil used herein is sheep oil. The sheep oil is yellow in color with a specific smell. To make the oil little softer, the oil is kept at room temperature for sometimes. Heating of oil is avoided as it may affect the treatment process. The heated animal oil may have bad effects on the reactions. The oil is used in an amount equal to the amount of combined powder. Oil is produced from sheep. It is a kind of local oil which is produced specifically in Mashhad. The other types of animal oil wouldn't be useful in the process. This is a kind of unique oil with a specific production process which makes it different from any other animal oils in other parts of the world.

According to the embodiments herein, one teaspoon of curcuma longa powder and one tea spoon of corncokle plant powder are mixed with a predetermined amount of animal oil. The animal oil used herein is equal to an amount of the combined powder, according to an embodiment herein. The oil used herein is in a sufficient quantity, according to one embodiment herein. The medicine is in the form of a liquid.

According to the embodiments herein, the prepared combination is kept in a room temperature (27° C.) for about 24 hour without any alternation, before using for treatment. According to an embodiment herein, the combination is kept at room temperature for 24 hours after use for the treatment. The prepared drug or the combination is kept in a closed glass bottle for 24 hours for extraction. The contents are mixed by shaking the bottle properly before taking out for treatment.

FIG. 1 shows a block diagram illustrating the various steps of preparing a herbal medicine for curing the infertility of a woman, according to an embodiment herein. With respect to FIG. 1, a corncockle powder is prepared by grinding the seeds of a corncockle plant and sifting the grinded seeds through a fine cloth (101). A turmeric powder is prepared by grinding the fried roots of turmeric and sifting the grinded roots through a fine cloth (102). The corncockle powder and the turmeric powder are mixed with an animal oil to form a mixture (103). The mixture is kept at room temperature for 24 hrs before using it for treatment (104).

According to the embodiments herein, the medicine is to be given in the vagina of the patient. The medicine is to be given immediately on the very same night the menstrual cycle of the patient ends. The standard intake of medicine is 2 cc. According to the embodiments herein, the dose is increased to 4 cc and further, when 2 cc of drug is not proven effective. The medicine is given using a syringe without its needle, in other words just the plastic part of the syringe is used. FSI is the scientific name of a drug or medicine.

The medicine is given after finishing of menstrual period immediately the very same night for two nights consecutively. During these two nights, the patient does not have sexual intercourse and does not micturate (pass urine) till morning The patient does not take medicine for next two consecutive days (the third and the fourth day) and also avoid sexual intercourse. The patient does not take medicine on the fifth day but the patient must do sexual intercourse on fifth day. The patient avoids micturition till morning on the fifth day.

In the course of treatment using the herbal medicine, the feet of the patient is held up and the head is put down. Then the patient bends her feet in 90 degree for 40 minutes to 1 hour. The patient does not sleep for 4 to 5 hours on that night. After the usage of medicine, the patient does not urinate till morning and does not sleep until an elapse of 3 hours after the injection. A plastic bed-sheet is used in the bed, and after each time of using the drug, patient should use a sanitary napkin.

Some of the patients will conceive in the first month. But some will not, so the amount of dose is increased from 2 cc to 4 cc for the next month. The patient is given a dose of 4 cc of the drug in the same manner for the next month. For example, 4 cc in first night, 4 cc in second night but doesn't cohabitate or encounter sexual intercourse without urination till morning. Patient doesn't use this drug and doesn't cohabitate in third and forth night. Patient doesn't use drug but does cohabitate and doesn't go to toilette until morning.

According to an embodiment, when the usage of the drug for two nights is not effective, then the drug is taken for three consecutive nights. The amount of drug is increased to 6 cc.

According to an embodiment herein, 4 cc at the first night and 4 cc of the medicine at the second night is used. At the fifth night, the patient doesn't use medicine but also doesn't have sexual intercourse and does not urinate because this substance is slab and is used to make the infertile womb ready to accept the spermatozoon.

According to one embodiment herein, if the first usage is not effective, the medicine is applied for the second time. In the second month, 6 cc of the medicine instead of 4 cc is applied. This amount of medicine is injected by two 6 cc syringes. It is effective for a patient whose infertility term is more than 14 years up to 20 years, according to an embodiment herein.

The medicine prepared in the embodiments herein has anti-inflammatory and antibacterial effect. The medicine cause to remove microbes from the vagina and facilitates entrance of sperm and prevent any security reactions against sperm and formation of anti-sperm-anti-body complex.

This mixture (turmeric+Corncockle) is effective on sterility treatment. The drug effects after treatment. The vaginal area isn't a sterile one. It includes the different kinds of microbes so the sterility of the sample isn't needed. The method of providing medicine is by injection way 4 days after period.

EXPERIMENTAL DATA

All sterile persons with uncertain reasons referred to The Asalian Hospital of Khorramabad for remedy during a year have been studied in this research. These persons have undergone all tests related to the scrutiny, a searching examination or investigation, of their sterility including tubal reasons (got via HCG—human chorionic gonadotropin), normal reasons containing ovulation reasons (via tests) and the occurrence of ovulation (via sonographic), mannish reasons (the test of normal sperm liquid) and biopsy, uterine reasons (via ondometer) and normal laparoscopy to refuse endometriosis and basin reasons. The reason of sterility is unknown and this upset the patient. The probable reasons related to the problem indirectly include social and cultural elements, the elements related to the render of services and the elements related to the illness. In this study, we don't have any sample group because all women that have been examined with different methods for pregnancy without any result were chosen. The kind of study is Case_Mordi. The statistical society herein refers to the women that take action for many years without any result. Regarding this, it was decided to find a scientific reason of it by studying a community and condidating two barren women with 18 and 11 years of sterility. Pregnancy was observed after a short period of time in these women after receiving this herbaceous medicine.

Example 1

To make the medicine, a teaspoon of powdery turmeric is mixed with a teaspoon of Corncockle (2 cc from each) and some animal oil in a sterile bottle at a room temperature for 24 h. After an interview, personal satisfaction and explanation of the new plants treatment, the patients are recommended to use the medicine after their menstrual cycle. After this time and before ovulation in the vagina, it is injected into the patient with a 4 cc syringe for 4 nights consecutively during two months. To absorb the drug, the patient has kept her pelvic (or the buttock) up for 40 minutes and then a pad is used by her. After 4 nights, the patient is allowed to have a compulsory sexual intercourse (during the medicine course she has to avoid intercourse), then the measure of expectancy is being studied in the samples and collected data is analyzed with suitable statistical methods (here case-mordi method).

Example 2

After an interview, personal satisfaction and explanation on the new plants treatment, these patients are recommended to use a medicine after their menstrual cycle. To make the medicine, a teaspoon of powdery turmeric is mixed with a teaspoon of Corncockle (3 cc from each) and some animal oil in a sterile bottle at a room temperature for 24 h. After this time and before ovulation in the vagina, it is injected into the patient with two syringes of 9 cc for 4 nights consecutively during one month. To absorb the drug, the patient has kept her pelvic (or the buttock) up for 40 minutes and then a pad is used by her. After 4 nights, the patient is allowed to have sexual intercourse compulsorily (during the medicine course she has to avoid intercourse), then the measure of expectancy is studied in the samples and collected data is analyzed with suitable statistical methods (here case-mordi method).

Example 3

After an interview, personal satisfaction and explanation on the new plants treatment, the patients are recommended to use a medicine after their menstrual cycle. To make the medicine, a teaspoon of powdery turmeric is mixed with a teaspoon of Corncockle (4 cc from each) and some animal oil in a sterile bottle at a room temperature for 24 h. After this time and before ovulation in the vagina, it is injected into the patient with two syringes of 4 cc for 5 nights consecutively during one month. To absorb the drug, the patient has kept her pelvic (or the buttock) up for 40 minutes and then a pad is used by her. After 4 nights, the patient is allowed to have a compulsory sexual intercourse (during the medicine course she has to avoid intercourse), then the measure of expectancy is being studied in the samples and collected data is analyzed with suitable statistical methods (here case-mordi method).

Example 4

After an interview, personal satisfaction and explanation on the new plants treatment, the patients are recommended to use a medicine after their menstrual cycle. To make the medicine, a teaspoon of powdery turmeric is mixed with a teaspoon of Corncockle (5 cc from each) and some animal oil in a sterile bottle at a room temperature for 24 h. After this time and before ovulation in the vagina, it is injected into the patient with two syringes of 5 cc for 5 nights consecutively during one month. To absorb the drug, the patient has kept her pelvic (or the buttock) up for 40 minutes and then a pad is used by her. After 4 nights, the patient is allowed to have a compulsory sexual intercourse (during the medicine course she has to avoid intercourse), then the measure of expectancy is being studied in the samples and collected data is analyzed with suitable statistical methods (here case-mordi method).

Example 5

After an interview, personal satisfaction and explanation on the new plants treatment, the patients are recommended to use a medicine after their menstrual cycle. To make the medicine, a teaspoon of powdery turmeric is mixed with a teaspoon of Corncockle (6 cc from each) and some animal oil in a sterile bottle at a room temperature for 24 h. After this time and before ovulation in the vagina, it is injected into the patient with two syringes of 6 cc for 5 nights consecutively during one month. To absorb the drug, the patient has kept her pelvic (or the buttock) up for 40 minutes and then a pad is used by her. After 4 nights, the patient is allowed to have a compulsory sexual intercourse (during the medicine course she has to avoid intercourse), then the measure of expectancy is being studied in the samples and collected data is analyzed with suitable statistical methods (here case-mordi method).

Example 6

After an interview, personal satisfaction and explanation on the new plants treatment, the patients are recommended to use a medicine after their menstrual cycle. To make the medicine, a teaspoon of powdery turmeric is mixed with a teaspoon of Corncockle (7 cc from each) and some animal oil in a sterile bottle at a room temperature for 24 h. After this time and before ovulation in the vagina, it is injected into the patient with two syringes of 7 cc for 5 nights consecutively during one month. To absorb the drug, the patient has kept her pelvic (or the buttock) up for 40 minutes and then a pad is used by her. After 4 nights, the patient is allowed to have a compulsory sexual intercourse (during the medicine course she has to avoid sexual intercourse), then the measure of expectancy is being studied in the samples and collected data is analyzed with suitable statistical methods (here case-mordi method).

Example 7

After an interview, personal satisfaction and explanation on the new plants treatment, the patients are recommended to use a medicine after their menstrual cycle. To make the medicine, a teaspoon of powdery turmeric is mixed with a teaspoon of Corncockle (8 cc from each) and some animal oil in a sterile bottle at a room temperature for 24 h. After this time and before ovulation in the vagina, it is injected into the patient with two syringes of 8 cc for 5 nights consecutively during one month. To absorb the drug, the patient has kept her pelvic (or the buttock) up for 40 minutes and then a pad is used by her. After 4 nights, the patient is allowed to have a compulsory sexual intercourse (during the medicine's course she has to avoid sexual intercourse), then the measure of expectancy is being studied in the samples and collected data is analyzed with suitable statistical methods (here case-mordi method).

Example 8

After an interview, personal satisfaction and explanation on the new plants treatment, the patients are recommended to use a medicine after their menstrual cycle. To make the medicine, a teaspoon of powdery turmeric is mixed with a teaspoon of Corncockle (9 cc from each) and some animal oil in a sterile bottle at a room temperature for 24 h. After this time and before ovulation in the vagina, it is injected into the patient with two syringes of 9 cc for 5 nights consecutively during one month. To absorb the drug, the patient has kept her pelvic (or the buttock) up for 40 minutes and then a pad is used by her. After 4 nights, the patient is allowed to have a compulsory sexual intercourse (during the medicine's course she has to avoid sexual intercourse), then the measure of expectancy is being studied in the samples and collected data is analyzed with suitable statistical methods (here case-mordi method).

Example 9

After an interview, personal satisfaction and explanation on the new plants treatment, these patients are recommended to use a medicine after their menstrual cycle. To make the medicine, a teaspoon of powdery turmeric is mixed with a teaspoon of Corncockle (10 cc from each) and some animal oil in a sterile bottle at a room temperature for 24 h. After this time and before ovulation in the vagina, it is injected into the patient with two syringes of 10 cc for 5 nights consecutively during one month. To absorb the drug, the patient has kept her pelvic (or the buttock) up for 40 minutes and then a pad has to be used by her. After 4 nights, the patient is allowed to have a compulsory sexual intercourse (during the medicine's course she has to avoid sexual intercourse), then the measure of expectancy is being studied in the samples and collected data is analyzed with suitable statistical methods (here case-mordi method).

The experiments showed the following results: the patients had sterility without certain reason and they became pregnant during the period of use of this medicine. A 26 year old woman with a period of sterility of 11 years became pregnant during the month of use of this medicine. A 27 year old woman with a period of sterility of 14 years, a 32 year old woman with a period of sterility of 8 years, became pregnant during the month of use of this medicine. A 36 year old woman with a period of sterility of 6 years became pregnant in 2 months of use of this the medicine.

Although the embodiments have been described in some detail by way of illustration and example for the purposes of clarity of understanding, it is clearly not limited thereby and this invention encompass any changes and modifications that may be practiced within the scope of the appended claims by ones skilled in the art.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims. It is also to be understood that the following claims are intended to cover all of the generic and specific features of the embodiments described herein and all the statements of the scope of the embodiments which as a matter of language might be said to fall there between.

What is claimed is:

1. A method of producing a medicine for treatment of infertility comprising steps of:
    making a corncockle powder from seeds of *Agrostemma githago*;
    making a turmeric powder from roots of *Curcuma longa*; and
    mixing the corncockle powder and the turmeric powder with an animal oil to form a liquid mixture, and wherein the animal oil is sheep oil; and
    keeping the liquid mixture at a room temperature for 24 hrs.

2. The method according to claim 1, wherein the step of making the corncockle powder includes separating a plurality of seeds of corncockle plant, drying the plurality of seeds of corncockle plant, grinding the dried plurality of seeds of corncockle plant and sifting the grinded plurality of seeds of corncockle plant to obtain a homogeneous corncockle powder, wherein the grinded plurality of seeds of corncockle plant are sifted using a mal-mal cloth.

3. The method according to claim 1, wherein the step of making the turmeric powder includes stirring and frying a plurality of roots of a turmeric plant and wherein the plurality of roots of turmeric plant are stirred-fried for 10 minutes till inflation, grinding the plurality of roots of a turmeric plant, and sifting the grinded plurality of roots of a turmeric plant to obtain a homogenous turmeric powder, wherein the grinded plurality of roots of a turmeric plant are sifted using a mal-mal cloth.

4. The method according to claim 1, wherein the mixing comprises mixing a teaspoon of the corncockle powder and a teaspoon of the turmeric powder with the animal oil.

\* \* \* \* \*